US012599340B2

(12) United States Patent　　(10) Patent No.:　US 12,599,340 B2
Thanikachalam et al.　　(45) Date of Patent:　Apr. 14, 2026

(54) SPATIOTEMPORAL-BASED DETECTION AND CORRECTION OF MOTION ARTIFACT FOR MEASUREMENT OF ARTERIAL PRESSURE WAVEFORM

(71) Applicant: Dynocardia, Inc., Newton, MA (US)

(72) Inventors: Mohan Thanikachalam, Newton, MA (US); Emily Upton, Cambridge, MA (US); Stamatios Aleiferis, Watertown, MA (US); Gokul Prasath Rajamanickam, Watertown, MA (US)

(73) Assignee: Dynocardia, Inc., Newton, MA (US)

( * ) Notice: Subject to any disclaimer, the term of this patent is extended or adjusted under 35 U.S.C. 154(b) by 0 days.

(21) Appl. No.: 18/763,848

(22) Filed: Jul. 3, 2024

(65) Prior Publication Data

US 2025/0009305 A1　　Jan. 9, 2025

Related U.S. Application Data

(60) Provisional application No. 63/525,519, filed on Jul. 7, 2023.

(51) Int. Cl.
　　*A61B 5/00*　　(2006.01)
　　*A61B 5/021*　　(2006.01)
　　*A61B 5/11*　　(2006.01)
(52) U.S. Cl.
　　CPC ........ *A61B 5/7214* (2013.01); *A61B 5/02108* (2013.01); *A61B 5/1102* (2013.01);
　　(Continued)

(58) Field of Classification Search
None
See application file for complete search history.

(56) References Cited

U.S. PATENT DOCUMENTS

| 4,409,983 A | * | 10/1983 | Albert | ............... | A61B 5/02438 |
| | | | | | 600/502 |
| 5,494,043 A | * | 2/1996 | O'Sullivan | ........ | A61B 5/02208 |
| | | | | | 600/500 |

(Continued)

FOREIGN PATENT DOCUMENTS

| WO | WO-2018148701 A1 | * | 8/2018 | ........... | A61B 5/0059 |
| WO | WO-2019195120 A1 | * | 10/2019 | ......... | A61B 5/02007 |
| WO | WO-2022035841 A1 | * | 2/2022 | ........... | A61B 5/0053 |

*Primary Examiner* — Meredith Weare
(74) *Attorney, Agent, or Firm* — ICE MILLER LLP; Justin D. Swindells

(57) ABSTRACT

A method and system for spatiotemporal management of motion artifacts/blood pressure drifts in an arterial pressure waveform. The system includes an elastomeric sensor array in touch with a surface patch of skin over a superficial artery of a subject, an actuator mounted over the elastomeric sensor array, and a camera mounted on the actuator to capture image data that a controller processes. The controller measures the arterial pressure waveform having motion artifacts caused by elastomeric sensor array deformation on the skin over the artery in the pulsatile area and over the skin adjacent to the artery in the non-pulsatile area. Further, the controller determines spatiotemporal information of the motion artifact in the pulsatile and non-pulsatile areas, correcting the arterial pressure waveform by removing the motion artifact based on the spatiotemporal information to determine the physiological parameters.

26 Claims, 7 Drawing Sheets

(52) U.S. Cl.
 CPC .......... *A61B 5/6833* (2013.01); *A61B 5/7225*
 (2013.01); *A61B 5/7257* (2013.01); *A61B*
 *2562/0247* (2013.01); *A61B 2562/164*
 (2013.01)

(56) References Cited

U.S. PATENT DOCUMENTS

| | | | |
|---|---|---|---|
| 10,398,383 B2 * | 9/2019 | van Dinther ....... | A61B 5/02416 |
| 11,690,513 B2 * | 7/2023 | Hu ...................... | A61B 5/6826 |
| | | | 600/476 |
| 2014/0058217 A1 * | 2/2014 | Giovangrandi ........ | A61B 5/721 |
| | | | 600/301 |
| 2015/0190063 A1 * | 7/2015 | Zakharov ............. | A61B 5/1107 |
| | | | 600/479 |
| 2016/0089042 A1 * | 3/2016 | Saponas ............. | A61B 5/02438 |
| | | | 600/407 |
| 2017/0325698 A1 * | 11/2017 | Allec ..................... | A61B 5/721 |
| 2019/0387972 A1 * | 12/2019 | Hu ...................... | A61B 5/7214 |
| 2021/0153755 A1 * | 5/2021 | Srinivasan ................ | G01L 1/24 |
| 2022/0211286 A1 * | 7/2022 | Tank .................... | A61B 5/6817 |
| 2022/0249026 A1 * | 8/2022 | Heneghan ............ | A61B 5/0022 |

* cited by examiner

SPATIOTEMPORAL-BASED DETECTION AND CORRECTION OF MOTION ARTIFACT FOR MEASUREMENT OF ARTERIAL PRESSURE WAVEFORM

CROSS-REFERENCE TO RELATED APPLICATIONS

This application claims benefit of priority to U.S. Provisional Patent Application No. 63/525,519 filed Jul. 7, 2023, which is hereby incorporated by reference in its entirety.

TECHNICAL FIELD OF THE INVENTION

The present invention relates to non-invasive periodic or continuous measurement of physiological parameters. More specifically, to use skin surface displacements and forces for spatiotemporal-based detection and correction of motion artifacts to accurately capture and assess arterial pressure (or other physiological phenomena) waveform despite movement.

BACKGROUND

The real-time capture of the arterial pressure waveform and its assessment to measure physiological parameters are essential for monitoring and assessing health inside and outside a medical facility. The physiological parameters are, but are not limited to, heart rate, blood pressure, respiratory rate, cardiac output, and other advanced hemodynamic parameters. The physiological parameters generally provide moment-to-moment information for making medical decisions during illness and operative procedures, as well as long-term information in helping to prevent and manage chronic diseases.

WO2019/195120A1 titled Tactile Blood Pressure Imager, which is incorporated by reference in its entirety herein, a Tactile Blood Pressure Imager (TBPI) includes an optomechanical force sensor array to measure skin deformation or displacement over a surficial artery such as the radial artery at a wrist of a patient. The TBPI provides a periodic and continuous measure of the arterial pressure waveform used to measure blood pressure, heart rate, respiratory rate, and advanced hemodynamic parameters. WO/2022/035841 entitled Optomechanical Method to Measure Arterial Pulse and Assess Cardiopulmonary Hemodynamics, which is incorporated by reference in its entirety here, discloses and discusses optomechanical sensor systems having structures and processes capable of measuring surface displacement due to arterial pressures.

During the measurement of the arterial pressure waveform, unintentional motion can induce mechanical forces that can lead to artifactual or inaccurate measurements of the arterial pressure waveforms. For example, regular operation of the device, wrist, hand, arm, body motions, or vibrational motions from vehicles or transport can generate artifactual forces that can corrupt an arterial pressure waveform, thus making it challenging to measure psychological parameters. Further, vibratory motions during patient transport may be of a similar frequency as the pulse. The movement of the hand, fingers, or other body parts can lead to a displacement of soft tissue and skin over the artery, which can corrupt the arterial pressure measurement. These motion artifacts cause a superposed deformation and displacement of the soft tissue and the skin leading to artifactual measurements of the arterial pressure waveform. A specific challenge presented by trying to isolate motion artifacts from a physiological signal such as one representing an arterial pressure is that the frequency of the motion artifact and the signal of interest can overlap, making it difficult to simply subtract out the artifact signal to reveal the signal of interest. Due to overlapping information in the spectral content of the signal of interest and the artifactual signal, isolating the artifactual signal from the signal of interest is not straightforward. Further complicating the isolation of the signal of interest is that over time tissue can relax, for example, which can cause a slow drift in the signal of interest, making it difficult to track over time while removing artifactual noise from the signal of interest. Thus, the aspects disclosed herein can account for not just motion artifacts but also blood pressure drift due to tissue relaxation.

The previously referenced patent applications offer no methods for mitigating these motion artifacts and blood pressure drift. Hence there is a need to detect and correct the motion artifacts/blood pressure drift to measure the arterial pressure waveform accurately.

SUMMARY

Without limiting the scope and details of the present disclosure as described herein, an important aspect of motion artifact/blood pressure drift correction techniques herein is that it takes into account effects on an area just outside or adjacent the pulsatile area (called "non-pulsatile" area herein) to eliminate or suppress these effects to provide a true and accurate representation of a physiological parameter, such as arterial pressure. In other words, the present disclosure does not look at the pulsatile area only; it inspects the area nearby to help isolate artifactual movements that corrupt or degrade a signal of interest such as blood pressure. A single sensor (e.g., an imaging device such as a camera) can be trained on the entire area comprising the pulsatile and non-pulsatile area, or multiple distinct sensors, such as two, can be each trained on the respective pulsatile and non-pulsatile areas with their outputs combined into a signal processor to determine the drift or motion artifact's contribution to or effect upon the signal of interest. Signal processing techniques disclosed herein are then used to characterize the motion artifact/drift and correct or compensate for it (e.g., by eliminating or suppressing its effect on the physiological waveform determination). When the physiological parameter being detected is blood pressure, for example, movements by the subject or transmitted to the subject (e.g., by external vibrations) can corrupt the blood pressure measurement, rendering its readings unreliable or untrustworthy. In cuff blood pressure systems, the subject must remain motionless and the arm should rest upon a stationary object that is not receiving any external movement forces such as vibrations. Aspects of the present disclosure allow for accurate readings of a physiological parameter to be made even while the area of measurement is moving or being subjected to external movement forces. Machine learning techniques refine the algorithm and signal processing to become better at detecting and removing motion artifacts/drift effects over time. According to another aspect herein, the sensing device is a simple imaging camera, which takes pictures or real-time images or videos of the undulating pulsations of skin, for example, as blood traverses through an artery. These images are processed by looking at both the pulsatile and non-pulsatile areas to isolate motion artifacts/drift effects and remove them from the signal.

In one aspect, the embodiments herein provide a method for the spatiotemporal management of motion artifacts in an arterial pressure waveform. The method includes receiving image data from an elastomeric sensor array made of elastomeric materials mounted over the undersurface of the actuator. The actuator is placed over the elastomeric sensor array, which is in touch with a subject's skin. The method includes measuring an arterial pressure waveform based on the image data. The arterial pressure waveform comprises motion artifacts caused by deformation of the elastomeric sensor array on the skin over an artery in a pulsatile area, and elastomeric sensor array deformation over the skin adjacent to the artery in a non-pulsatile area comprises motion artifacts but no arterial pressure waveform. Further, the method includes determining spatiotemporal information of the motion artifact in the pulsatile area and the non-pulsatile area, correcting the arterial pressure waveform by removing the motion artifact based on the spatiotemporal information and determining physiological parameters of the subject based on the corrected arterial pressure waveform.

In an embodiment, determining the spatiotemporal information of the motion artifact in the pulsatile area and the non-pulsatile area includes detecting the motion artifact in the pulsatile area, detecting the motion artifact in the non-pulsatile area, determining the spatiotemporal information of the motion artifact in the pulsatile area and the motion artifact in the non-pulsatile area.

In an embodiment, the pulsatile area and the non-pulsatile area are digitally separated by estimating a displacement of the image data at each time point, determining a variance of a signal over time-based on the displacement, performing a temporal Fourier transform of the displacement of the image data at all locations based on the variance of the signal over time, determining areas with the transformed displacement that meets a predefined threshold, and segmenting the areas with the transformed displacement that meet the predefined threshold into the pulsatile area and the areas with the transformed displacement that does not meet the predefined threshold into the non-pulsatile area.

In an embodiment, detecting the motion artifact in the non-pulsatile area includes determining a plurality of parameters associated with the non-pulsatile area, determining reference regions in the image data based on the plurality of parameters, filtering residual pulsatile signal from the reference regions, and detecting the motion artifact in the non-pulsatile area based on the filtered residual signal from the reference regions.

In an embodiment, the residual pulsatile signal is filtered from the reference regions by applying one of a median average filter, a moving median average filter, and a Fourier transform low pass filter.

In an embodiment, the plurality of parameters determines the reference region that surrounds the pulsatile area with adequate distance from the pulsatile area to remove the low-amplitude effects that arterial pressure waveform and a large possible area to maximize spatial pattern recognition used to impute the changes within the pulsatile area due to the artifactual motion.

In an embodiment, detecting the motion artifact in the non-pulsatile area based on the filtered residual signal from the reference regions includes determining a temporal derivative using a frequency filter and detecting the motion artifact in the non-pulsatile area based on the temporal derivative.

In an embodiment, detecting the motion artifact in the pulsatile area includes matching a template to detect changes in a pulse waveform morphology that trigger the high-frequency artifact flag and detecting the motion artifact in the pulsatile area based on the template.

In an embodiment, correcting the arterial pressure waveform by removing the motion artifact based on the spatiotemporal information includes detecting a type of motion artifact in the pulsatile area and the non-pulsatile area, detecting whether an artifact flag is raised, and applying a correction technique to remove the motion artifact from the arterial pressure waveform based on the spatiotemporal information, the raised artifact flag, and type of the motion artifact in the pulsatile area and the non-pulsatile area.

In another aspect, the embodiments herein provide a system for the spatiotemporal management of motion artifacts. The system includes a elastomeric sensor array made of elastomeric material in touch with a surface patch of a subject's skin, an actuator mounted on the top surface of the elastomeric sensor array, and a controller communicatively coupled to the light source, camera, and the actuator. The actuator has an actuated state in which a controlled amount of pressure isolates a spatiotemporal signal from an artery of the subject. The camera captures image data of the elastomeric sensor array. Based on the image data, the controller is configured to measure an arterial pressure waveform. The arterial pressure waveform comprises motion artifacts caused by elastomeric sensor array deformation on the skin over the artery in a pulsatile area and elastomeric sensor array deformation over the skin adjacent to the artery in a non-pulsatile area. The controller is configured to determine spatiotemporal information of the motion artifact in the pulsatile area and the non-pulsatile area, correct the arterial pressure waveform by removing the motion artifact based on the spatiotemporal data, and determine physiological parameters of the subject based on the corrected arterial pressure waveform.

In an embodiment, the elastomeric sensor array is mechanically separated by segmenting the elastomeric sensor array into a first sensor array and a second sensor array in touch with the subject's skin surface. The first sensor array and the second sensor array are separated at a predefined distance. The actuator is mounted over the first sensor array and a second sensor array. The first sensor array is mounted on the skin over the artery representing the pulsatile area, and the second sensor array is mounted over the skin adjacent to the artery representing the non-pulsatile area.

In an embodiment, the elastomeric sensor array and the actuator are mechanically separated by segmenting the elastomeric sensor array into a first sensor array and a second sensor array in touch with the subject's skin surface. The first sensor array and the second sensor array are separated at a predefined distance. The actuator is segmented into a first actuator mounted over the first sensor array representing the pulsatile area and a second actuator mounted over the second sensor array representing the non-pulsatile area.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the scope thereof, and the embodiments herein include all such modifications.

BRIEF DESCRIPTION OF FIGURES

The proposed spatiotemporal-based detection and correction of motion artifacts are illustrated in the accompanying drawings, throughout which like reference letters indicate corresponding parts in the various figures. The embodiments herein will be better understood from the following description with reference to the drawings in which.

Figure 1:
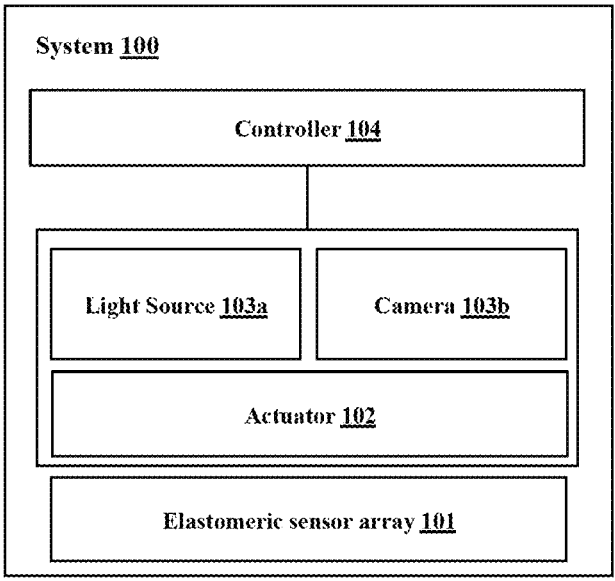
FIG. 1 illustrates an optomechanical system for spatiotemporal-based detection and correction of motion artifacts to accurately measure arterial pressure waveform, according to embodiments as disclosed herein.

To the extent possible, reference numerals have been used to represent like elements in the drawing. Further, those of ordinary skill in the art will appreciate that elements in the drawing are illustrated for simplicity and may have yet to be drawn to scale. For example, the dimension of some of the elements in the drawing may be exaggerated relative to other elements to help to improve the understanding of aspects of the invention. Furthermore, conventional symbols may have represented the elements in the drawing. Finally, the drawings may show only those specific details pertinent to the understanding of the embodiments of the invention so as not to obscure the drawing with details that will be readily apparent to those of ordinary skill in the art having the benefit of the description herein.

DETAILED DESCRIPTION OF INVENTION

The implementations herein and the various features and advantageous details thereof are explained more fully with reference to the non-limiting implementations that are illustrated in the accompanying drawings and detailed in the following description. It should be understood, however, that the following descriptions, while indicating preferred implementations and numerous specific details thereof, are given by way of illustration and not of limitation. Many changes and modifications may be made within the scope of the implementations herein without departing from the spirit thereof, and the implementations herein include all such modifications. The examples used herein are intended merely to facilitate an understanding of ways in which the implementations herein can be practiced and to further enable those skilled in the art to practice the implementations herein. Accordingly, the examples should not be construed as limiting the scope of the implementations herein.

Descriptions of well-known components and processing techniques are omitted to avoid unnecessarily obscuring the implementations herein. Also, the various implementations described herein are not necessarily mutually exclusive, as some implementations can be combined with other implementations to form new implementations.

Referring now to the drawings, and more particularly to FIGS. 1 through 7, where similar reference characters denote corresponding features consistently throughout the figures. FIG. 1 illustrates an optomechanical system 100 for spatiotemporal-based detection and correction of motion artifacts to accurately measure arterial pressure waveform, according to embodiments as disclosed herein. The optomechanical sensor 100 includes an elastomeric sensor array 101, an optional actuator 102, a light source 103a, a camera 103b, and a controller 104. Although in this example, the sensor array is an elastomeric sensor array, the present disclosure contemplates other types of sensor arrays including sensors comprising piezoresistive materials or substrates or other materials or devices capable of being deformed in response to movement of skin from within the body.

The elastomeric sensor array 101 is in touch with or directly contacts a surface patch of a subject's skin 106, and the actuator is mounted over the elastomeric sensor array 101. The elastomeric sensor array 101 forms the interface between the actuator 102 and the skin 106. Under the skin is the soft tissue 107, and under the soft tissue is the bone 108. In other aspects, the sensor array has a material or substrate that can deform in response to movements of the skin, and the substrate or material is sensitive enough to move flexibly and conformally with the movements of the skin. The idea here is to exaggerate the skin movements or to translate them to the substrate/material so that those movements can be picked up by the camera 103b as, for example, spatiotemporal information.

The actuator 102 is mounted over the elastomeric sensor array 101. In an embodiment, the actuator 102 is a control balloon. The actuator 102 is inflated to achieve an actuated state in which a controlled amount of pressure isolates a spatiotemporal signal from an artery of the subject.

In an embodiment, the optomechanical sensor system 100 is described herein.

The elastomeric sensor array 101 is mounted under the surface of the actuator 102. The underlying skin 106 deformations or displacement leads to deformation or displacement of the elastomeric sensor array 101. The camera 103b captures the spatiotemporal elastomeric sensor array deformation as a continuous video (image data) with sub-millimeter resolution.

Controller 104 is communicatively coupled to optomechanical sensor system 100. Controller 104 is configured to measure an arterial pressure waveform based on the image data. The arterial pressure waveform comprises motion artifacts caused by elastomeric sensor array deformation on the skin over the artery in a pulsatile area and elastomeric sensor array deformation over the skin adjacent to the artery in a non-pulsatile area. A non-pulsatile area can be an area immediately adjacent to or adjacent to an area of the skin under which the artery is present. The non-pulsatile area does not overlap with the pulsatile area such that no part of the non-pulsatile area is immediately over the artery of interest. No appreciable artery signal or skin deformation caused by a pulsing artery is detectable in the non-pulsatile area. In other words, the artery pulse is so weak or non-existent in the non-pulsatile area such that the sensor array is not able to reliably detect or determine a physiological parameter therefrom. Depending on the weight and height of the subject, the non-pulsatile area can be located a predetermined distance away from the pulsatile area. For example, the non-pulsatile area can be located 1 mm, 2 mm, 3 mm, 4 mm, 5 mm, 6 mm, 7 mm, 8 mm, 9 mm, 10 mm, or between 11-15 mm, or between 15-25 mm away from the artery. Those familiar with human physiology will appreciate that a pulsatile area is an area where a physiological parameter can be detected reliably. A non-pulsatile area is an area where such parameter is not detectable at all, or not detectable in any reliable manner (e.g., a weak pulse may be present, but too weak to measure reliably). The Controller 104 is configured to determine spatiotemporal information of the motion artifacts in the pulsatile area and in the non-pulsatile area, correct the arterial pressure waveform by removing or suppressing the motion artifact based on the spatiotemporal information (including in particular the motion artifact in the non-pulsatile area), and determine physiological parameters of the subject based on the corrected arterial pressure waveform.

During regular operation, the motion of the device, wrist, hand, arm, or body motions or external vibrational motions from vehicles or transport (e.g., inside an ambulance or emergency vehicle or an airplane) can generate unwanted artifactual forces within the pulsatile area that can corrupt or degrade the arterial pressure waveform, thus making it challenging to measure psychological parameters, including blood pressure. Further, the motion artifactual forces within the pulsatile area may have a similar temporal profile as the arterial pressure waveform of interest, thus making it difficult to differentiate between actual changes in physiological parameters versus those due to spurious changes caused by artifacts. The vibratory motions during patient transport may be of a similar frequency as the arterial pressure waveform (signal of interest), making them difficult to isolate from the signal of interest. Also, the motions of the hand or fingers can lead to the displacement of the soft tissue 107 and skin 106 over the artery 109 at the wrist over the course of seconds, which is on the same time scale as the arterial pulse waveform. These motion artifacts cause a superposed deformation and displacement of the elastomeric sensor array and can lead to artifactual measurements of the arterial pulse waveform (and thereby inaccurate measurements) if correction is not performed. Hence controller 104 measures the elastomeric sensor array deformation or displacement not only on the skin over the artery 109 with arterial pulsation (pulsatile area) but also over the skin adjacent to the artery 109 without the arterial pulsation (non-pulsatile area). In an embodiment, the elastomeric sensor array 101 is separated into the pulsatile area and the non-pulsatile area either digitally or mechanically. The digital separation of the elastomeric sensor array 101 is described with respect to the FIG. 2, while the mechanical separation is described with reference to FIGS. 3-4.

In an embodiment, the force sensory array system 200 is described herein.

The force sensor array 201 can be made of piezoresistive materials and is mounted under the surface of the actuator 202. The underlying skin 106 deformations lead to deformation or displacement of the displaceable elements in the force sensor array 201. The controller 203 has a high-resolution analog to digital converter data acquisition system that captures the data from all the array elements and converts the captured data into a digital image as shown in the FIG. 5.

In an embodiment, the force sensory array system 200 is described herein.

The force sensor array 201 made of piezoresistive materials can be mounted directly on top of (e.g., in direct contact with) the skin 106. The sensor system 200 can be held together using a strap 202a or equivalent system, which is used to provide a retain force and to increase the counter force on the artery by tightening the strap 202a. The underlying skin 106 deformations lead to deformation or displacement of the elements in the force sensor array 201. The force sensory array 201 described herein can alternately be one of the following: Capacitive sensor array, force sensing resistor array, or load cell array. The controller 203 has a data acquisition system that captures the data from all the array elements, a transducer that converts the change in resistance or capacitance from each element into an analog voltage, and a high-resolution analog to digital converter that converts the analog signal into a digital signal. The digital signal when organized into an array forms a digital image as shown in the FIGS. 5-6. The same process described above can be used to process the data.

A primary underpinning of the proposed disclosure is the recognition that the forces that lead to artifactual deformation and displacement affect both the pulsatile area 110 and the non-pulsatile area 111 of the elastomeric sensor array 101, while physiological changes that lead to changes in the arterial waveform are primarily confined to the pulsatile area 110. Thus, using spatial information from the non-pulsatile area 111, the artifactual deformations, independent of the physiological changes, can be captured, quantified, and used to correct the arterial pulse waveform.

Figure 2:
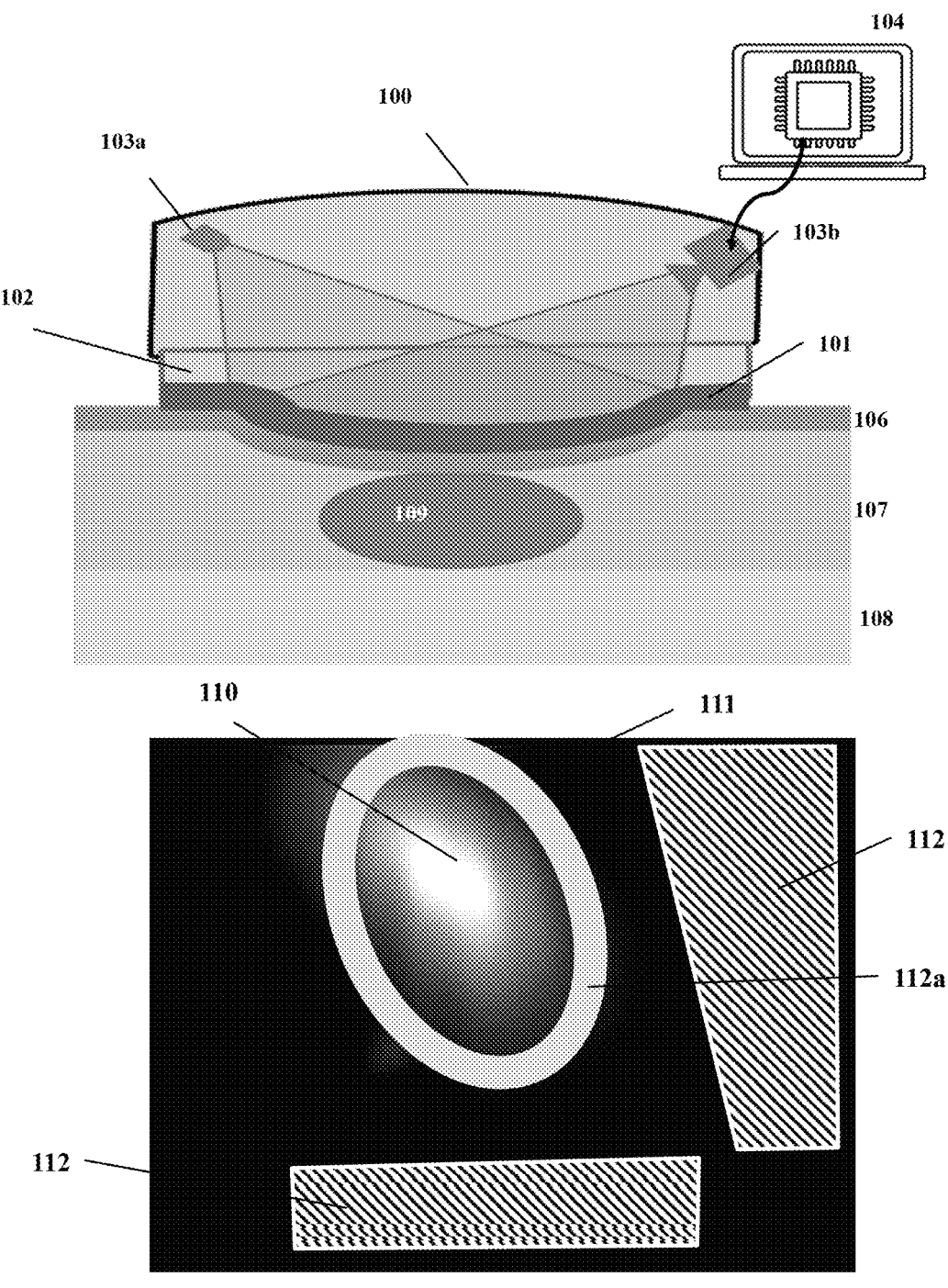
FIG. 2 illustrates a scenario in which digital separation of the elastomeric sensor array is performed, accordingly to embodiments as disclosed herein.

FIG. 2 illustrates a scenario in which digital separation of the elastomeric sensor array 101 is performed accordingly to embodiments as disclosed herein. The optomechanical system 100, as described in FIG. 1, is in touch with skin 106. The layer of soft tissue 107 under the skin 106 is in touch with bone 108. The layer of soft tissue 107 includes artery 109. The optomechanical system 100 measures the deformation or displacement on the skin over the artery 109 with arterial pulsation (referred pulsatile area 110) and also over the skin adjacent to the artery without the arterial pulsation (referred to as non-pulsatile area 111).

The elastomeric sensor array deformation on skin 106 over artery 109 in the pulsatile area 110 is caused due to physical forces generated from the pulsation of artery 109. It is transmitted to soft tissue 107 and skin 106 over artery 109. This elastomeric sensor array deformation or displacement is continuously captured by camera 103b as the image data. In one embodiment, a computer vision engine present in controller 104 transforms the image data into a linear temporal signal by first estimating the motion due to the underlying pulse, then localizing the pulse by integrating motion vectors, and then segmenting it as shown in FIG. 2. The segmented image 110 is then analyzed to find the average displacement and estimate the arterial pressure waveform.

The pulsatile region 110 and the non-pulsatile area 111 region are first delineated. A goal is to separate the elastomeric sensor array 101 digitally into the pulsatile region or area 110 and the non-pulsatile area 111. To detect the motion artifacts in the pulsatile region 110 and in the non-pulsatile region 111, digital separation of the pulsatile region 110 and the non-pulsatile region 111 can be performed by estimating a displacement of the image data at each time point, determining a variance of a signal over time, based on the displacement, performing a temporal Fourier transform of the displacement of the image data at all locations based on the variance of the signal over time, determining areas with the transformed displacement that meets a predefined threshold, and segmenting the areas with the transformed displacement that meet the predefined threshold into the pulsatile area 110 and the areas with the transformed displacement that does not meet the predefined threshold into the non-pulsatile area 111.

In an embodiment, detecting the motion artifact in the non-pulsatile area includes determining a plurality of parameters associated with the non-pulsatile area, determining reference regions 112 in the image data based on the plurality of parameters, filtering residual pulsatile signal from the reference regions 112, and detecting the motion artifact in the non-pulsatile area 111 based on the filtered residual signal from the reference region 112. The residual pulsatile signal is filtered from the reference region 112 by applying a median average filter, a moving median average filter, and a Fourier transform low pass filter.

In an example, in the case of a single elastomeric sensor array 101, the pulsatile area 110 is identified by first: (A) estimating the displacement of the image ($\Delta x$, $\Delta y$) at each time point t. (B) Secondly, the variance of the signal over time $V(x, y, t) = [<\Delta x(t)^2> + <\Delta y(t)^2>]^{1/2}$ and temporal Fourier transform of the displacement of the image at all locations $F(x, y, w) = F[\Delta x(t), \Delta y(t)]$. (C) Finally, thresholding the area with sufficient power under the cardiac frequencies (~40 BPM-200 BPM) allows segmentation of the pulsatile area 110, where the physiological signal is present.

The non-pulsatile area 111 is generally defined as the area of the elastomeric sensor array outside of the pulsatile area 110. the non-pulsatile area 111 can be further refined into reference regions 112, which consists of specific areas of the non-pulsatile area 111 used for digital signal subtraction. In particular, these reference regions 112 are chosen to have specific additional properties that improve motion detection for motion correction. The selection of the reference regions 112 includes multiple parameters. One of the reference regions 112a surrounds the pulsatile area 110 based on the parameters that include adjacency to the pulsatile area 110 to capture deformations in the elastomeric sensor array as close to the pulsatile area 110 as possible and at the same time, adequate distance from the pulsatile area 110 to remove the low-amplitude effects that may be due to the actual physiological signal, and as large as a possible area to maximize spatial pattern recognition used to impute the changes within the pulsatile area 110 due to artifactual motion (also referred as motion artifact). Despite using these parameters, there may be some residual arterial pulsation causing deformation in the reference areas 112. As a result, the residual pulsatile signal needs to be filtered out. In one embodiment, a moving median average filter is applied directly to the image before estimating elastomeric sensor array deformation. Alternatively, a median average filter can be applied directly to the linear physiological signal that is output by the device, with a window length determined by the heart rate of the subject under investigation. Additional approaches include temporal Fourier transform of the signal and low pass filtering beneath the heart rate.

Figure 3:
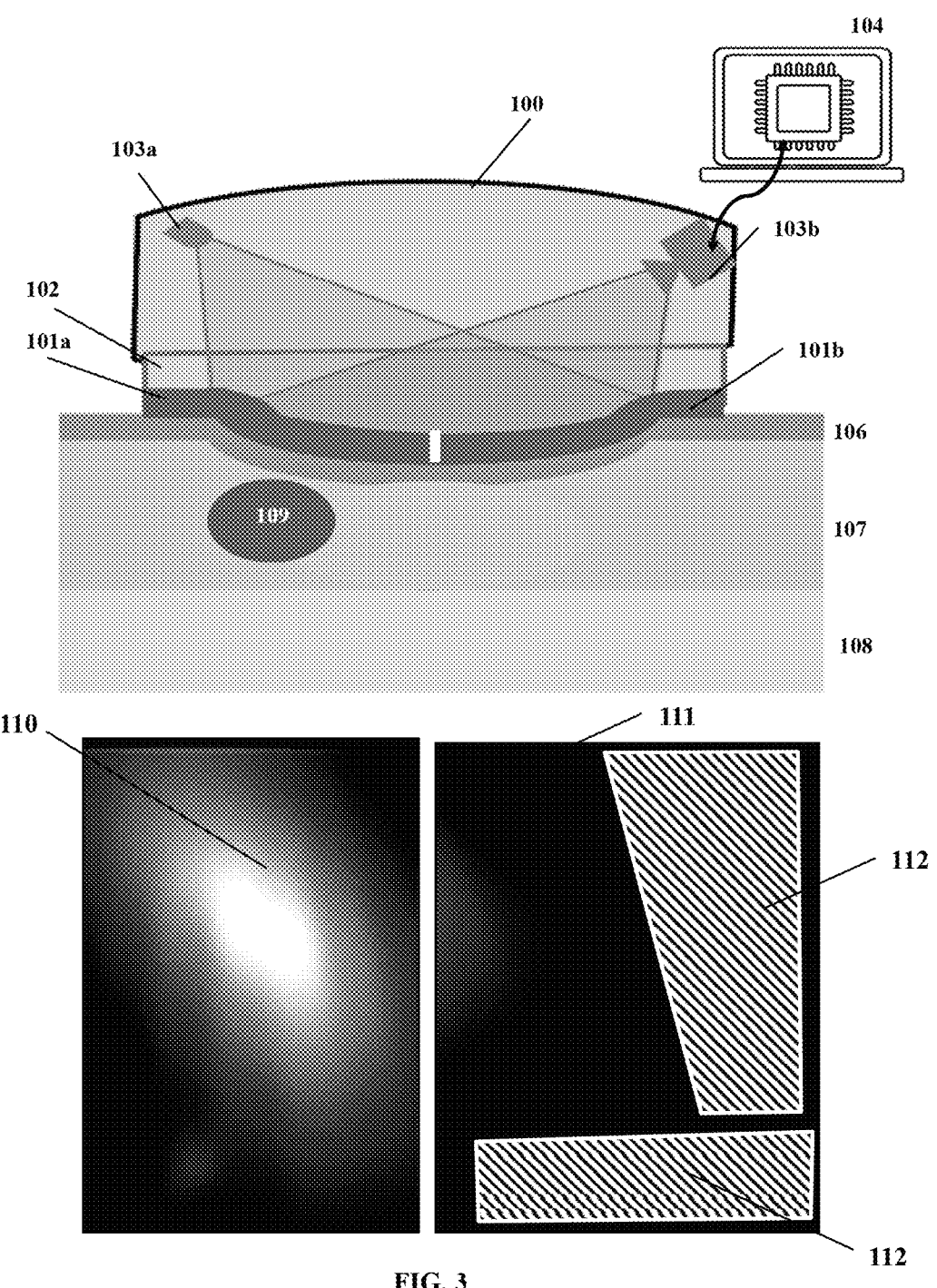
FIG. 3 illustrates a scenario in which the elastomeric sensor array is mechanically separated, accordingly to embodiments as disclosed herein.

FIG. 3 illustrates a scenario in which the elastomeric sensor array 101 is mechanically separated, accordingly to embodiments as disclosed herein. In an embodiment, the elastomeric sensor array 101 is mechanically separated as a first elastomeric sensor array 101a and a second elastomeric sensor array 101b. A single actuator 102 is mounted over the first elastomeric sensor array 101a and the second elastomeric sensor array 101b and is optically accessible by a single camera 103b.

In this embodiment, one elastomeric sensor array 101a is placed over the artery 109, isolating mechanical forces due to arterial pulsation to the first elastomeric sensor array 101a and thus representing the pulsatile area 110. The physically separate second elastomeric sensor array 101b is then, by design, adjacent to (but not contacting) the artery 109 and is defined as the non-pulsatile area 111 without arterial pulsation. The pulsatile and non-pulsatile areas, 110 and 111, will have deformations reflective of global artifactual motions from the subject. The elastomeric sensor array 101 is split into any ratio (for example, the pulsatile elastomeric sensor array having 75% of the camera's view and the non-pulsatile elastomeric sensor array having 25% of the visual view). Alternately, a second camera (not shown but in the area of light source 103a) can be arranged such that the camera 103b is trained on the pulsatile area and the second camera is trained on the non-pulsatile area. While their fields of view may overlap, each camera is focused on an area within the respective pulsatile and non-pulsatile areas. The non-pulsatile area represents an area where skin movement is not impacted by blood passing through the artery 109. The skin in the non-pulsatile area may move for other reasons (e.g., bending of the wrist), but these movements are not related to the arterial waveform of interest.

Figure 4:
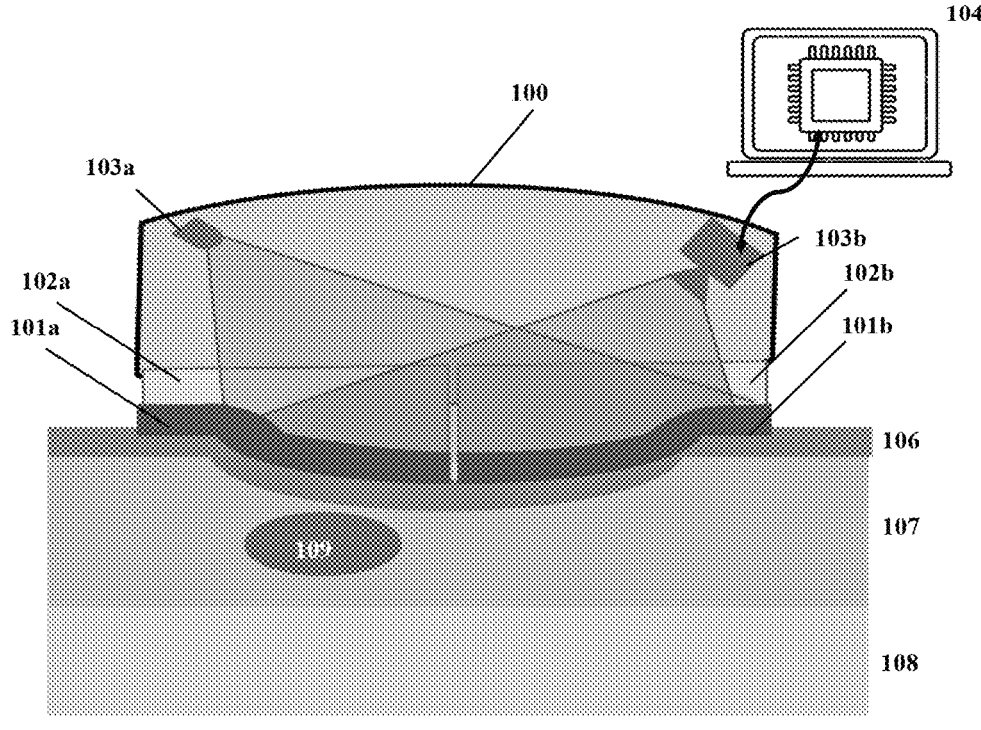
FIG. 4 illustrates a scenario in which both the elastomeric sensor array and actuator are mechanically separated, accordingly to embodiments as disclosed herein.
Figure 4:
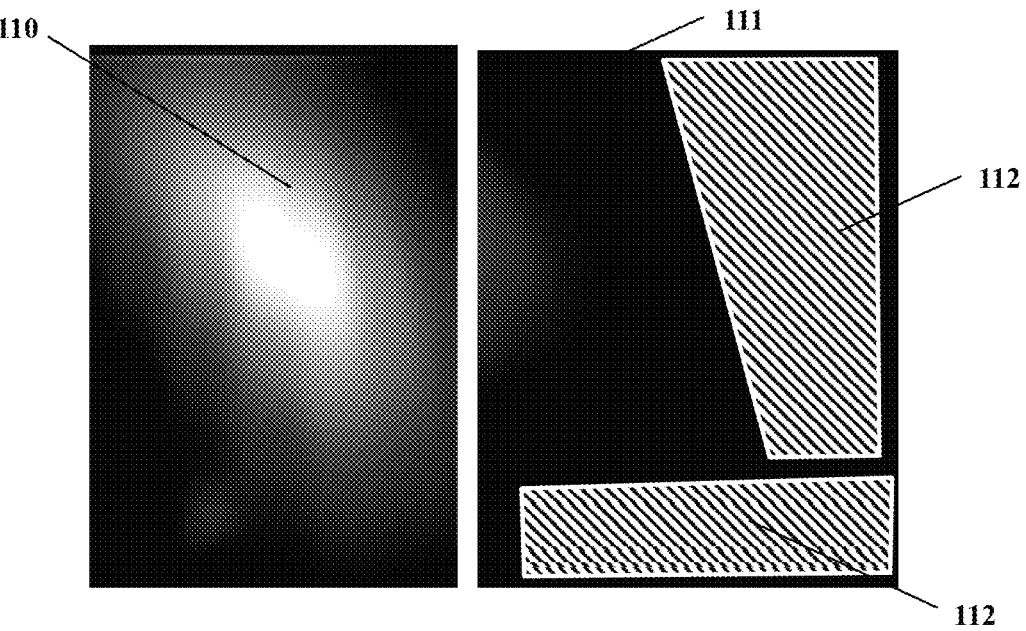

FIG. 4 illustrates a scenario in which the elastomeric sensor array 101 and actuator 102 are mechanically separated (e.g., distinct hardware device structures), accordingly to embodiments as disclosed herein. In an embodiment, the elastomeric sensor array 101 is separated as a first elastomeric sensor array 101a and a second elastomeric sensor array 101b. The first elastomeric sensor array 101a and the second elastomeric sensor array 101b are separated. The actuator 102 is separated as a first actuator 102a mounted over the first elastomeric sensor array 101a representing the pulsatile area 110 and a second actuator 102b mounted over the first elastomeric sensor array 101b representing the non-pulsatile area 111.

In this example, the elastomeric sensor array 101 is mechanically separated and pneumatically actuated using two separate actuators, 102a and 102b, respectively, and is optically accessible by a single camera 103b (or alternately by a second camera as discussed above). One elastomeric sensor array 101a is placed over artery 109, and the entire elastomeric sensor array 101a is defined as the pulsatile area 110. The second physically separate elastomeric sensor array 101b is then, by design, adjacent to artery 109 and represents the non-pulsatile area 111. The non-pulsatile area is an area near the artery where deformations of the skin are not caused by blood passing through the artery, but can be caused by other human-caused or external events, such as a bending of the wrist or waving of the hand or external vibrations transmitted to the non-pulsatile area of the skin. The elastomeric sensor array 101 is split into any ratio (for example, the pulsatile elastomeric sensor array having 75% of the camera's view and the non-pulsatile elastomeric sensor array having 25% of the visual view). Similarly, the actuator 102 is split into any ratio.

Figure 5:
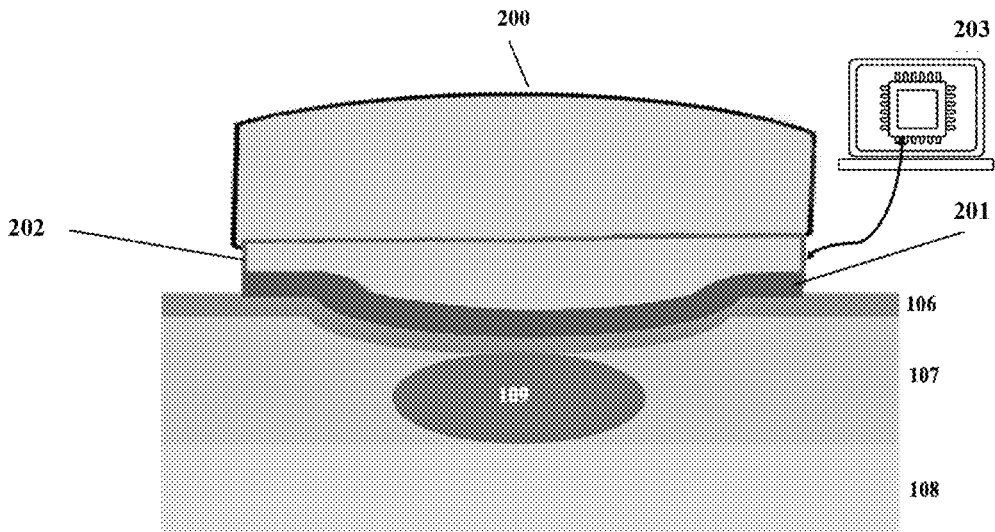
FIG. 5 illustrates a force sensor array system for spatiotemporal-based detection and correction of motion artifacts to accurately measure arterial pressure; illustrates a scenario in which a digital separation of a force sensory array is performed, and an actuator is used to apply force/pressure on the artery, accordingly to embodiments as disclosed herein.
Figure 5:
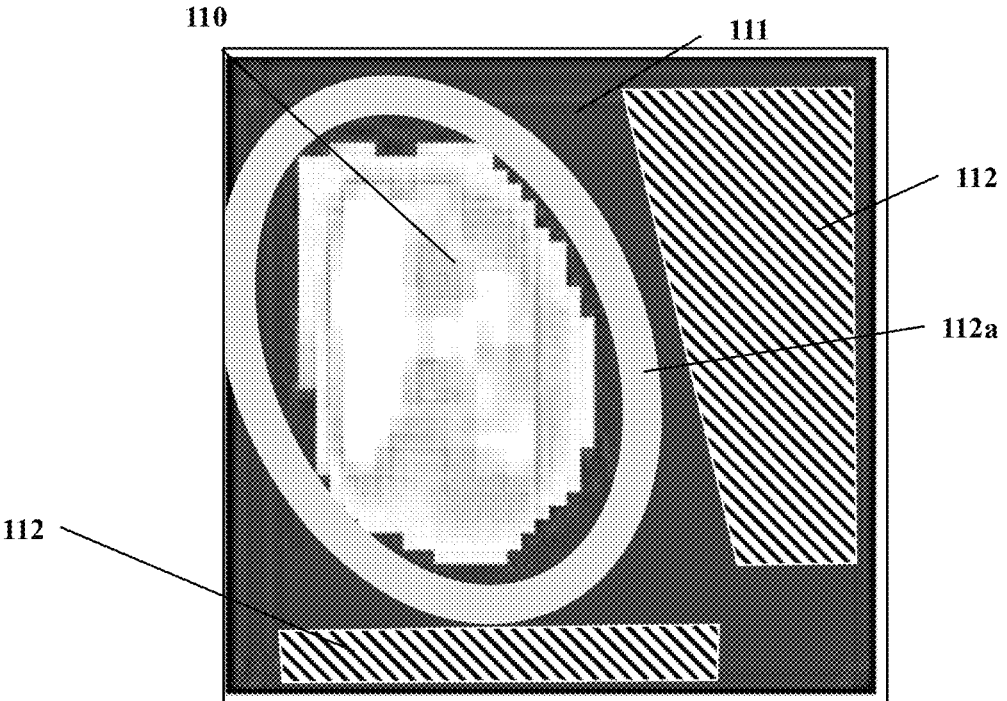
Figure 6:
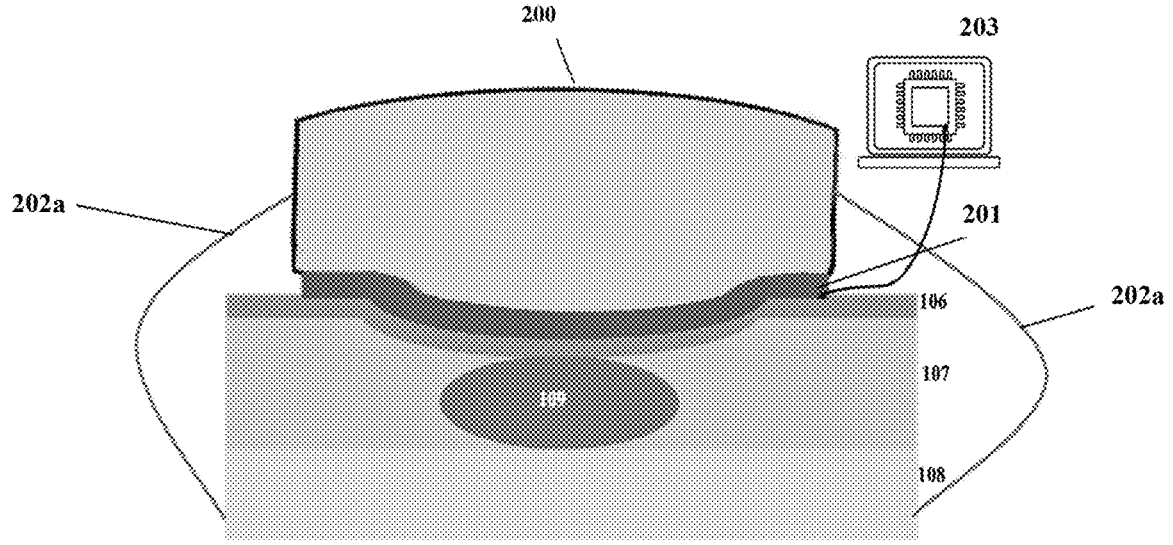
FIG. 6 illustrates a force sensor array system for spatiotemporal-based detection and correction of motion artifacts to accurately measure arterial pressure; illustrates a scenario in which a digital separation of a force sensory array is performed, and a strap system is used to apply force/pressure on the artery instead of an actuator, accordingly to embodiments as disclosed herein.
Figure 6:
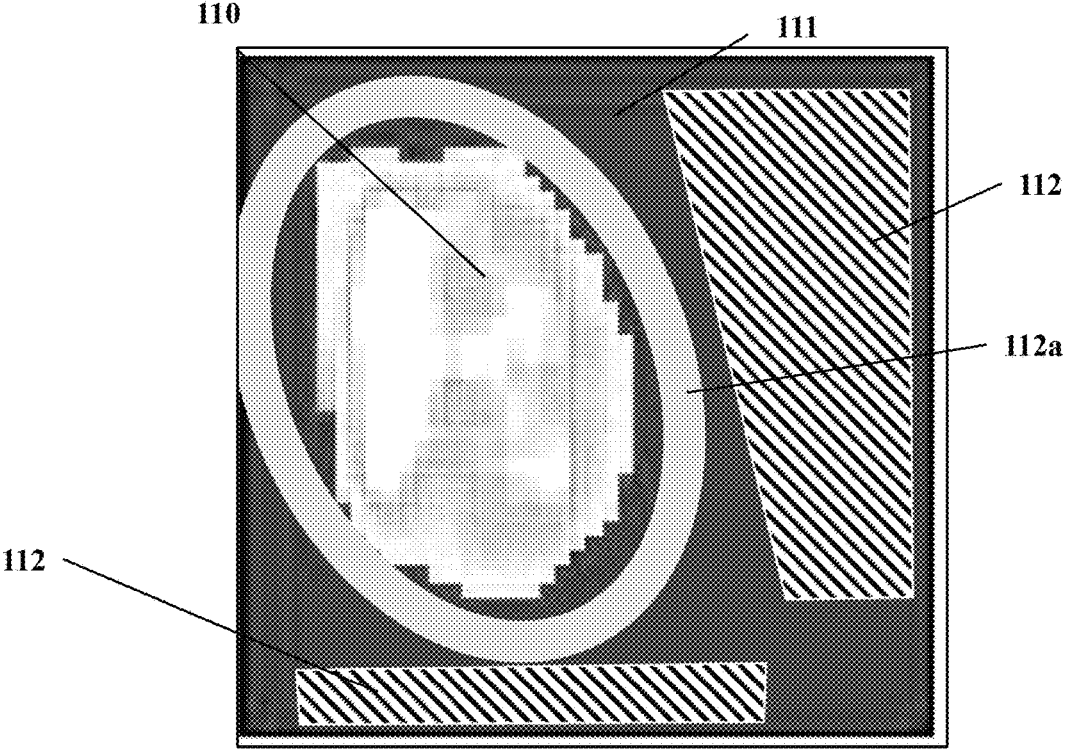
Figure 7:
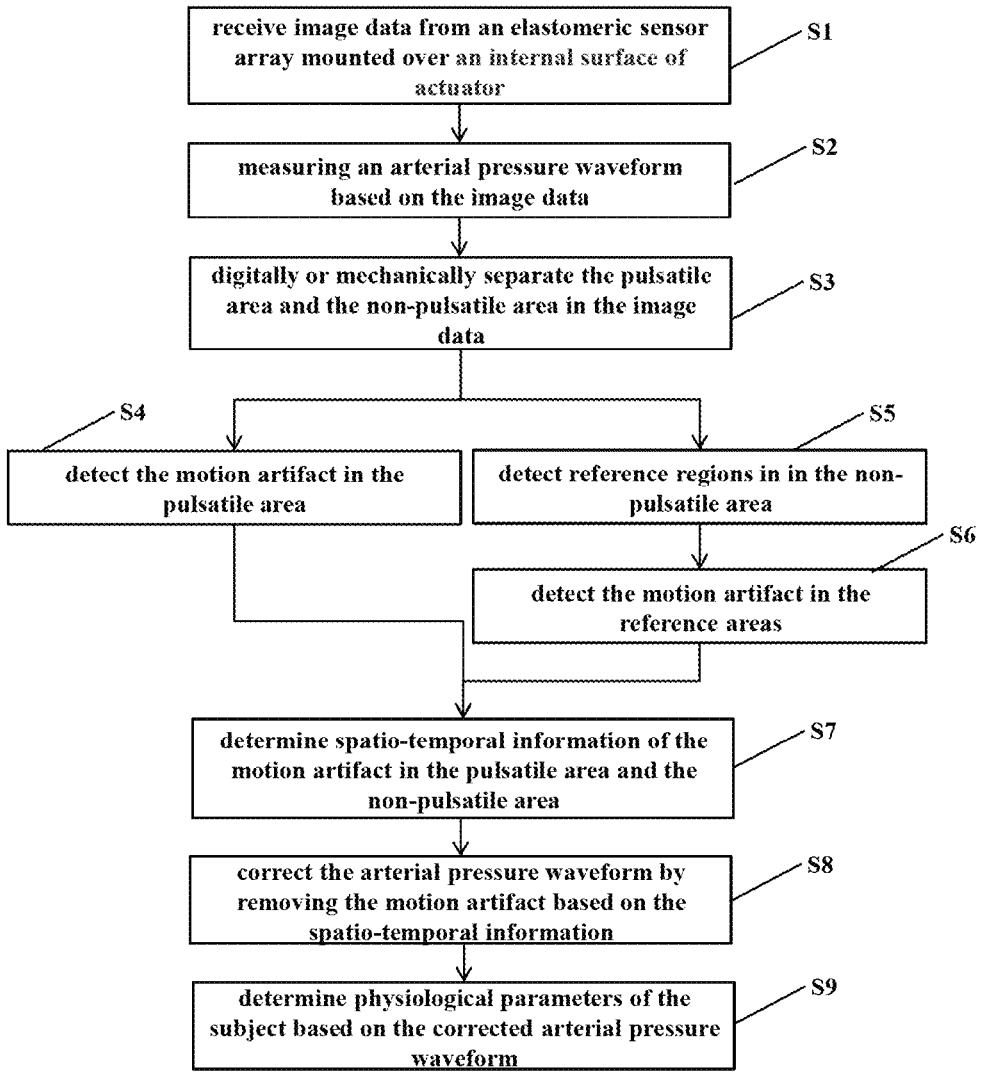
FIG. 7 is a flow chart illustrating a method for spatiotemporal-based detection and correction of motion artifacts to measure arterial pressure waveform, according to embodiments disclosed herein.

FIG. 5 illustrates a method for spatiotemporal-based detection and correction of motion artifacts to measure arterial pressure waveform, according to embodiments as disclosed herein. At step S1, the method includes receiving image data from the elastomeric sensor array (sensor array) 103 mounted undersurface of the actuator 102. The elastomeric sensor array 101 is in touch with the skin of the subject. The actuator has an actuated state in which a controlled amount of pressure isolates a spatiotemporal signal or other signal from an artery of the subject. The elastomeric sensor array 101 deformation is captured as image data by camera 103*b*.

In step S2, the method includes measuring an arterial pressure waveform based on the image data. The arterial pressure waveform comprises motion artifacts caused by elastomeric sensor array deformation on the skin over an artery in a pulsatile area and elastomeric sensor array deformation over the skin adjacent to the artery in a non-pulsatile area. In an embodiment, generating the arterial pressure waveform based on the image data includes transforming the image data into a linear temporal signal and generating the arterial pressure waveform based on the linear temporal signal.

At step S3, the method includes digitally or mechanically separating the pulsatile area 110 and the non-pulsatile area 111 in the image data. The digital separation of the pulsatile area 110 and the non-pulsatile area 111 are described with respect to FIG. 2. The mechanical separation of the pulsatile area 110 and the non-pulsatile area 111 are described with respect to the FIGS. 3-4.

At step S4, the method includes detecting the motion artifact in the pulsatile area 110. In an embodiment, the motion artifact in the pulsatile area 110 matches a template to detect changes in a pulse waveform morphology that trigger the high-frequency artifact flag.

At step S5, the method includes detecting the motion artifact in the non-pulsatile area 111 and, in an embodiment, detecting reference regions 112 in the image data.

The non-pulsatile area 111 can be further refined into reference regions, consisting of specific areas of the non-pulsatile area 111 used for digital signal subtraction. In particular, these reference regions 112 are chosen to have specific additional properties that improve motion detection and motion correction. The selection of the reference region includes multiple parameters, such as an adjacency to the pulsatile area to capture the elastomeric sensor array deformations, a distance from the pulsatile area to remove low-amplitude, and a length of the pulsatile area.

At step S6, the method includes detecting the motion artifact in the non-pulsatile area 111. In an embodiment, the residual pulsatile signal from the reference regions 112 is filtered by applying one of a median average filter, a moving median average filter, and a Fourier transform low pass filter. Then, the motion artifact in the non-pulsatile area 111 is detected based on the filtered residual signal from the reference region 112.

In step S7, the method includes determining spatiotemporal information of the motion artifact in the pulsatile area and the non-pulsatile area. The motion artifacts described herein fall into two categories: (1) high-frequency artifacts and (2) slow drift of blood pressure caused by, for example, tissue relaxation. (1) High-frequency artifacts are detected using a frequency filter and by computation of a temporal derivative.

In an embodiment, a spatial approach is used for motion artifact detection in the non-pulsatile region 111. Once reference region 112 is identified in the non-pulsatile area 111, reference region 112 is analyzed to detect the motion artifacts in the non-pulsatile area 111.

In an embodiment, a temporal approach is used for motion artifact detection in the pulsatile region 110. It is the temporal method for detecting high-frequency artifacts within the pulsatile area 110. The high-frequency artifact detection includes template matching to detect changes in pulse waveform morphology that trigger the high-frequency artifact flag. Frequency and derivative cutoffs and beat templates are derived from an extensive data set of artifacts that have been acquired. These cutoffs are updated as additional artifact data is added to a database.

The net displacement of the reference region 112 is fed into a voter model that accumulates votes of increased or decreasing over time. Votes are exponentially down-weighted based on how distant in the past they are. A drift flag is raised once a pre-defined threshold has been met. In addition, a dictionary of spatial artifact patterns is generated offline using an extensive data set of artifactual data. The spatial displacement patterns in the entire elastomeric sensor array are compared to the motion artifact dictionary. If the spatial pattern match exceeds a predefined threshold, an artifact flag is also raised.

In step S7, the method includes correcting the arterial pressure waveform by removing the motion artifact based on the spatiotemporal information. Correcting the arterial pressure waveform includes detecting a type of motion artifact in the pulsatile area and the non-pulsatile area, detecting whether an artifact flag is raised, and applying a correction technique to remove the motion artifact from the arterial pressure waveform based on the spatiotemporal information, the raised artifact flag, and type of the motion artifact in the pulsatile area and the non-pulsatile area.

In an embodiment, a spatial approach for motion artifact correction is used. Once an artifact flag has been raised, a correction technique is applied to the arterial pressure waveform. The selection and use of a particular correction technique depend on the specific type of artifact flag and the spatial pattern of the motion artifact.

In the case of a high-frequency artifact, the motion artifact detector keeps the flag in an on state until the motion artifact has resolved. Suppose the motion artifact length is less than a pre-defined threshold. In that case, the new physiological signal is calibrated to the most recent high-fidelity signal prior to the motion artifact.

In the case of drift of blood pressure due to tissue relaxation, which typically occurs slowly, the signal from the reference region 112 and the pulsatile area 110 are compared. An optimization routine is used to find coefficients A and B that are multiplied by the displacements in the reference area, i.e., $A*\Delta x^{ref}$, $B \Delta y^{ref}$ that minimize the mean squared error between the pulsatile signal and the scaled reference signal over a pre-defined period of time. This initial correction technique uses a reference region with maximal spatial separation from the pulsatile area 110. If the mean squared error cannot be achieved, then the spatial pattern in the reference region 112 is matched to a dictionary of artifactual deformations. A larger reference region is used to maximize the motion artifact's spatial signature. The spatial signal is projected on the dictionary component $g(x, y)$ to determine a coefficient $\mu$ such that $\mu*g(x^{ref}, y^{ref})=(\Delta x^{ref}, \Delta y^{ref})$. The dictionary component is then used to compute the corrected signal by $(\Delta x^{corr}, \Delta y^{corr})=(\Delta x^{puls}, \Delta y^{pulse})-\mu \ g(x^{pulse}, y^{pulse})$. If the motion artifact is not sufficiently similar to a predefined dictionary element, then the reference area is interpolated into the pulsatile area using a polynomial interpolation $h(x,y)$. The corrected signal is then estimated by $(\Delta x^{corr}, \Delta y^{corr})=(\Delta x^{puls}, \Delta y^{pulse})-h(x^{pulse}, y^{pulse})$.

The net result of the motion artifact pipeline is to determine the correction in the pulsatile area based on spatiotemporal information of the non-pulsatile area. The primary difference between the techniques presented here and prior described techniques results from differences in the spatial manifestation of artifacts on the elastomeric sensor array. Previously described techniques in digital video stabilization utilize a reference area for the correction of camera jitter, for example. These techniques generally rely on the motion that affects the camera alone, leading to artifacts manifesting in the foreground or background of the image as relatively simple affine transformations. These simple motions from the reference area can be directly subtracted out. Because motion artifacts do not just affect the camera but also an elastomeric sensor array, motion artifacts are more spatially complex. As a result, the underly camera jitter techniques do not hold and do not allow for ready application for motion correction, necessitating the development of the techniques described above. In particular, the motion correction techniques use spatial and temporal information to determine a reference area and sophisticated spatial reconstruction techniques to perform error correction on the pulsation area.

At step S9, the method includes determining the physiological parameters of the subject based on the corrected arterial pressure waveform. In an embodiment, once error correction has been performed, the physiological parameters can be estimated as described in PCT Patent Application Publication No. WO2022/035841A1, titled Optomechanical Method to Measure Arterial Pulse and Assess Cardiopulmonary Hemodynamics, filed on 10 Aug. 2021. The motion artifact correction process yields additional changes in the device output.

Machine learning techniques can be employed to improve motion artifact removal with a high degree of accuracy. A learning model is created from videos showing pulsation only and from other videos without pulsation but with motion artifacts (e.g., hand or wrist motion). The model is trained to isolate the pulse signal of interest only, and adaptively learns to discriminate motion artifacts from the signal of interest and select only the pulsatile signal. Artifact detection and drift correction are also augmented by the model. For example, in the case of drift in blood pressure caused by, for example, relaxation of the tissue surrounding the pulsatile area, the coefficients for the optimization routine discussed above can be adjusted by the model, and additionally or alternately the dictionary of artifactual deformations can be updated or modified based on a drift model that communicates with the learning model to determine how accurately the drift has been corrected to isolate the pulsatile signal of interest from the motion artifacts.

The foregoing description of the specific implementations will so fully reveal the general nature of the implementations herein that others can, by applying current knowledge, readily modify and/or adapt for various applications without departing from the generic concept, and, therefore, such modifications and adaptations should and are intended to be comprehended within the meaning and range of equivalents of the disclosed implementations. It is to be understood that the phraseology or terminology employed herein is for the purpose of description and not of limitation. Therefore, while the implementations herein have been described in terms of preferred implementations, those skilled in the art will recognize that the implementations herein can be practiced with modification within the spirit and scope of the implementations as described herein.

What is claimed is:

1. A method for correction of motion artifacts affecting a physiological waveform, the method comprising the steps of:
   receiving image data from a sensor array configured to be in contact with a skin of a subject;

analyzing the image data to characterize a physiological waveform that includes motion artifact caused by movement of a body part of the subject or an external movement imparted to the subject, which has an effect (a) on sensor array deformation or movement on the skin over an artery in a pulsatile area in response to an external positive pressure being applied thereto and (b) on sensor array deformation or movement over the skin adjacent to the artery in a non-pulsatile area;
determining information relating to the motion artifact affecting the pulsatile area and the non-pulsatile area;
correcting the physiological waveform by removing or suppressing the motion artifact based on at least the information relating to the motion artifact in the non-pulsatile area to produce a corrected physiological waveform; and
determining physiological parameters of the subject based on the corrected physiological waveform that does not include the motion artifact based on at least the information relating to the motion artifact in the non-pulsatile area,
wherein the correcting the physiological waveform includes:
   detecting a type of motion artifact present in the pulsatile area and in the non-pulsatile area;
   detecting whether an artifact flag is raised responsive to the detecting the type of motion; and
   applying a correction technique to remove the motion artifact from the physiological waveform based on at least the information, the raised artifact flag, and the type of the motion artifact present in the pulsatile area and in the non-pulsatile area.

2. The method, as claimed in claim 1, wherein the physiological waveform is representative of an arterial pressure, and wherein the determining the information comprises:
   detecting a characteristic of the motion artifact in the pulsatile area;
   detecting the characteristic or another characteristic of the motion artifact in the non-pulsatile area;
   determining the information of the motion artifact in the pulsatile area and the motion artifact in the non-pulsatile area.

3. The method as claimed in claim 2, wherein the sensor array being trained on both the pulsatile area and the non-pulsatile area, the method further comprising digitally separating by a controller the pulsatile area and the non-pulsatile area in the image data by:
   estimating a displacement of the image data at each time point;
   determining a variance of a signal over time based on the displacement;
   performing a temporal Fourier transform of the displacement of the image data at all locations based on the variance of the signal over time;
   determining areas with the transformed displacement that meet a predefined threshold; and
   segmenting the areas with the transformed displacement that meet the predefined threshold into the pulsatile area and the areas with the transformed displacement that does not meet the predefined threshold into the non-pulsatile area.

4. The method, as claimed in claim 2, wherein the detecting the characteristic or another characteristic of the motion artifact in the non-pulsatile area comprises:
   determining a plurality of parameters associated with the non-pulsatile area;

determining at least one reference region in the image data based on the plurality of parameters associated with the non-pulsatile area;

filtering out a residual pulsatile signal from at least one reference region to produce a pulse-free reference signal; and detecting the characteristic or another characteristic of the motion artifact in the non-pulsatile area based on the pulse-free reference signal from at least one reference region.

5. The method, as claimed in claim 4, wherein the residual pulsatile signal is filtered out from the at least one reference region by applying one of a median average filter, a moving median average filter, and a Fourier transform low pass filter.

6. The method as claimed in claim 4, wherein the determining the at least one reference region in the image data based on the plurality of parameters associated with the non-pulsatile area includes identifying at least one reference region that surrounds the pulsatile area with adequate distance from the pulsatile area to remove low-amplitude effects that the arterial pressure waveform and a large as possible area to maximize spatial pattern recognition used to impute the changes within the pulsatile area due to the artifactual motion.

7. The method, as claimed in claim 4, wherein the detecting the characteristic or another characteristic of the motion artifact comprises:

determining a temporal derivative using a frequency filter; and detecting the characteristic or another characteristic of the motion artifact in the non-pulsatile area based on the temporal derivative.

8. The method, as claimed in claim 2, wherein the detecting the characteristic of the motion artifact in the pulsatile area comprises:

matching a beat template to detect changes in a morphology of the arterial pressure waveform, which changes trigger a high-frequency artifact flag.

9. The method, as claimed in claim 1, wherein the analyzing the image data comprises:

transforming the image data into a linear temporal signal; and generating the physiological waveform based on the linear temporal signal.

10. The method of claim 1, wherein the physiological waveform is an arterial pressure waveform, and wherein the information is spatiotemporal information.

11. The method of claim 1, wherein the physiological waveform is or is representative of a heart rate, a blood or arterial pressure, a respiratory rate, a cardiac output, or a hemodynamic parameter.

12. The method, as claimed in claim 1, wherein the sensor array is an elastomeric sensor array, the elastomeric sensor array being mounted over an internal surface of an actuator, wherein the actuator is over the elastomeric sensor array.

13. A system for management of a motion artifact, comprising:

a sensor array configured to be in contact with a surface patch of a skin of a subject, the system having a camera that captures image data of the sensor array; and a controller, communicatively coupled to the camera, configured to:

measure an arterial pressure waveform based on the image data, wherein the arterial pressure waveform comprises a motion artifact caused by movement of a body part of the subject or an external movement imparted to the subject, which has an effect on a respective deformation or movement of the sensor array on the skin over (a) the artery in a pulsatile area in response to positive pressure being applied thereto and over (b) the skin adjacent to the artery in a non-pulsatile area, determine information relating to the motion artifact affecting the pulsatile area and the non-pulsatile area, correct the arterial pressure waveform by removing the motion artifact based on the determined information to produce a corrected arterial pressure waveform, and determine the physiological parameters of the subject based on the corrected arterial pressure waveform in which the motion artifact is suppressed based on at least the information relating to the motion artifact in the non-pulsatile area, wherein the information of the motion artifact in the pulsatile area and the non-pulsatile area is determined by:

detecting the motion artifact in the pulsatile area;

detecting the motion artifact in the non-pulsatile area; and determining spatiotemporal information of the motion artifact in the pulsatile area and in the non-pulsatile area, wherein the system captures image data of both the pulsatile area and the non-pulsatile area from the sensor array, the controller being further configured to digitally separate the pulsatile area and the non-pulsatile area in the image data by:

estimating a displacement of the image data at each time point;

determining a variance of a signal over time based on the displacement;

performing a temporal Fourier transform of the displacement of the image data at all locations based on the variance of the signal over time;

determining areas with the transformed displacement that meet a predefined threshold; and segmenting the determined areas with the transformed displacement that meet the predefined threshold into the pulsatile area and the areas with the transformed displacement that does not meet the predefined threshold into the non-pulsatile area.

14. The system, as claimed in claim 13, wherein the detecting the motion artifact in the non-pulsatile area comprises:

determining a plurality of parameters associated with the pulsatile area;

determining a reference region in the image data based on the plurality of parameters associated with the pulsatile area;

filtering out a residual pulsatile signal from the reference region to produce a pulse-free reference signal; and detecting the motion artifact in the non-pulsatile area based on the pulse-free reference signal from the reference region.

15. The system, as claimed in claim 14, wherein the residual pulsatile signal is filtered out from the reference region by applying one of a median average filter, a moving median average filter, or a Fourier transform low pass filter.

16. The system, as claimed in claim 14, wherein the plurality of parameters comprises one or more of an adjacency to the pulsatile area to capture the sensor array deformations, a distance from the pulsatile area to remove low-amplitude effects associated with the arterial pressure waveform, or a length of the pulsatile area.

17

17. The system, as claimed in claim 14, wherein the detecting the motion artifact in the non-pulsatile area based on the pulse-free reference signal from the reference region, comprises:

determining a temporal derivative using a frequency filter; and detecting the motion artifact in the non-pulsatile area based on the temporal derivative.

18. The system, as claimed in claim 13, wherein the detecting the motion artifact in the pulsatile area comprises:

matching a template to detect changes in a morphology of the arterial pressure waveform, which changes trigger a high-frequency artifact flag.

19. The system, as claimed in claim 13, wherein the correcting the arterial pressure waveform comprises:

detecting a type of motion artifact present in the pulsatile area and the non-pulsatile area;

detecting whether an artifact flag is raised; and applying a correction technique to remove the motion artifact from the arterial pressure waveform based on at least the information, the raised artifact flag, and the type of motion artifact in the pulsatile area and the non-pulsatile area.

20. The system, as claimed in claim 13, wherein the measuring the arterial pressure waveform based on the image data, comprises:

transforming the image data into a linear temporal signal; and generating the arterial pressure waveform based on the linear temporal signal.

21. The system, as claimed in claim 13, wherein the sensor array deformation or movement on the skin over the artery in the pulsatile area is caused at least in part due to physical forces generated from the pulsation of the artery and is transmitted to soft tissue and the skin over the artery.

22. The system, as claimed in claim 13, wherein the physiological waveform is an arterial pressure waveform, and wherein the information is spatiotemporal information.

23. The system, as claimed in claim 13, wherein the sensor array is an elastomeric sensor array, the system further comprising an actuator having an actuated state in which a controlled amount of pressure isolates a spatiotemporal signal from an artery of the subject.

24. A method for correction of motion artifacts affecting a physiological waveform, the method comprising the steps of:

receiving image data from a sensor array configured to be in contact with a skin of a subject;

analyzing the image data to characterize a physiological waveform that includes motion artifact caused by movement of a body part of the subject or an external movement imparted to the subject, which has an effect (a) on sensor array deformation or movement on the skin over an artery in a pulsatile area in response to an external positive pressure being applied thereto and (b) on sensor array deformation or movement over the skin adjacent to the artery in a non-pulsatile area;

determining information relating to the motion artifact affecting the pulsatile area and the non-pulsatile area;

correcting the physiological waveform by removing or suppressing the motion artifact based on at least the information relating to the motion artifact in the non-pulsatile area to produce a corrected physiological waveform; and determining physiological parameters of the subject based on the corrected physiological waveform that does not include the motion artifact based on at least the information relating to the motion artifact in the non-pulsatile area, wherein the physiological waveform is representative of an arterial pressure, and wherein the determining the information comprises:

detecting a characteristic of the motion artifact in the pulsatile area;

detecting the characteristic or another characteristic of the motion artifact in the non-pulsatile area;

determining the information of the motion artifact in the pulsatile area and the motion artifact in the non-pulsatile area, wherein the sensor array is trained on both the pulsatile area and the non-pulsatile area, the method further comprising digitally separating by a controller the pulsatile area and the non-pulsatile area in the image data by:

estimating a displacement of the image data at each time point;

determining a variance of a signal over time based on the displacement;

performing a temporal Fourier transform of the displacement of the image data at all locations based on the variance of the signal over time;

determining areas with the transformed displacement that meet a predefined threshold; and segmenting the areas with the transformed displacement that meet the predefined threshold into the pulsatile area and the areas with the transformed displacement that does not meet the predefined threshold into the non-pulsatile area.

25. A method for correction of motion artifacts affecting a physiological waveform, the method comprising the steps of:

receiving image data from a sensor array configured to be in contact with a skin of a subject;

analyzing the image data to characterize a physiological waveform that includes motion artifact caused by movement of a body part of the subject or an external movement imparted to the subject, which has an effect (a) on sensor array deformation or movement on the skin over an artery in a pulsatile area in response to an external positive pressure being applied thereto and (b) on sensor array deformation or movement over the skin adjacent to the artery in a non-pulsatile area;

determining information relating to the motion artifact affecting the pulsatile area and the non-pulsatile area;

correcting the physiological waveform by removing or suppressing the motion artifact based on at least the information relating to the motion artifact in the non-pulsatile area to produce a corrected physiological waveform; and determining physiological parameters of the subject based on the corrected physiological waveform that does not include the motion artifact based on at least the information relating to the motion artifact in the non-pulsatile area, wherein the physiological waveform is representative of an arterial pressure, and wherein the determining the information comprises:

detecting a characteristic of the motion artifact in the pulsatile area;

detecting the characteristic or another characteristic of the motion artifact in the non-pulsatile area;

determining the information of the motion artifact in the pulsatile area and the motion artifact in the non-pulsatile area, wherein the detecting the characteristic of the motion artifact in the non-pulsatile area comprises:

determining a plurality of parameters associated with the non-pulsatile area;

determining at least one reference region in the image data based on the plurality of parameters associated with the non-pulsatile area;

filtering out a residual pulsatile signal from at least one reference region to produce a pulse-free reference signal; and detecting the characteristic of the motion artifact in the non-pulsatile area based on the pulse-free reference signal from at least one reference region.

26. A system for management of a motion artifact, comprising:

a sensor array configured to be in contact with a surface patch of a skin of a subject, the system having a camera that captures image data of the sensor array; and a controller, communicatively coupled to the camera, configured to:

measure an arterial pressure waveform based on the image data, wherein the arterial pressure waveform comprises a motion artifact caused by movement of a body part of the subject or an external movement imparted to the subject, which has an effect on a respective deformation or movement of the sensor array on the skin over (a) the artery in a pulsatile area in response to positive pressure being applied thereto and over (b) the skin adjacent to the artery in a non-pulsatile area, determine information relating to the motion artifact affecting the pulsatile area and the non-pulsatile area, correct the arterial pressure waveform by removing the motion artifact based on the determined information to produce a corrected arterial pressure waveform, and determine the physiological parameters of the subject based on the corrected arterial pressure waveform in which the motion artifact is suppressed based on at least the information relating to the motion artifact in the non-pulsatile area, wherein the correcting the arterial pressure waveform comprises:

detecting a type of motion artifact present in the pulsatile area and the non-pulsatile area;

detecting whether an artifact flag is raised; and applying a correction technique to remove the motion artifact from the arterial pressure waveform based on at least the information, the raised artifact flag, and the type of motion artifact in the pulsatile area and the non-pulsatile area.

* * * * *